United States Patent [19]

Gerharz

[11] 4,324,459

[45] Apr. 13, 1982

[54] OPTICAL TEST PATTERN

[75] Inventor: Reinhold Gerharz, Bethesda, Md.

[73] Assignee: The United States of America as represented by the Secretary of the Army, Washington, D.C.

[21] Appl. No.: 114,866

[22] Filed: Jan. 24, 1980

[51] Int. Cl.$^3$ .................. A61B 3/02; G01M 11/00
[52] U.S. Cl. ................................ 351/32; 356/124.5
[58] Field of Search .................. 351/32, 36, 37; 356/124.5

[56] References Cited

U.S. PATENT DOCUMENTS 2,463,813   3/1949   Shepard ........................... 351/32

OTHER PUBLICATIONS

Luckiesh, Test Charts Representing a Variety of Visual Tasks, 1944, American Journ. of Opht.
Ronchi et al., Some Remarks on Ophthalmic Test Types, Jun. 1972, American Journal of Optometry.

Primary Examiner—John K. Corbin
Assistant Examiner—Rodney B. Bovernick
Attorney, Agent, or Firm—Nathan Edelberg; Milton W. Lee; Aubrey J. Dunn

[57] ABSTRACT

A stelliform arrangement of sectors each having a uniform optical density and with different sectors having different optical densities.

2 Claims, 1 Drawing Figure

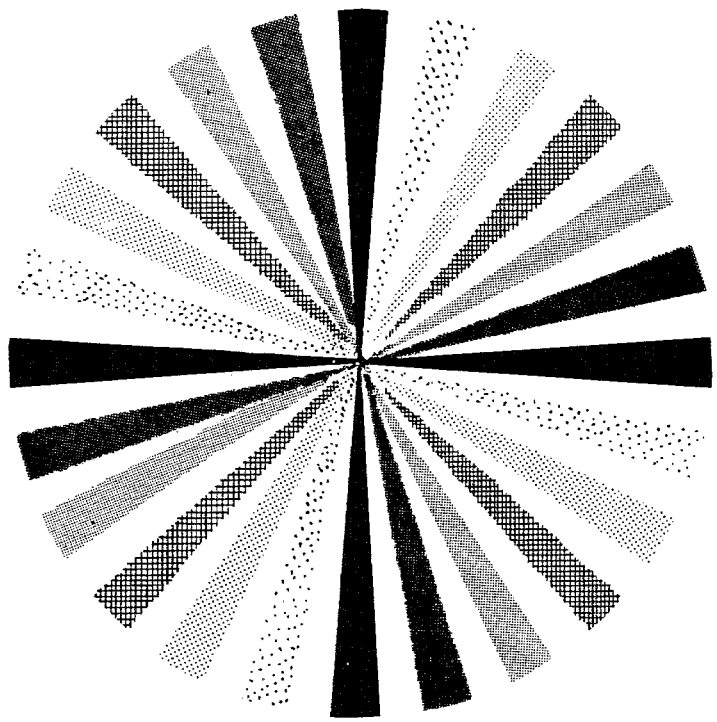

OPTICAL TEST PATTERN

The invention described herein may be manufactured, used and licensed by the U.S. Government for governmental purposes without the payment of any royalties thereon.

BACKGROUND OF THE INVENTION

1. Field of the Invention

This invention is in the field of test patterns for optical systems, in particular those patterns from which one may determine such qualities of an optical system as resolution or transfer function.

2. Description of the Prior Art

Various devices and methods are currently desired for testing the quality of optical elements and/or optical paths between such elements. A typical method uses a pattern of opaque shapes on a white or transparent background. Perhaps the most familiar are the various methods used for testing human vision. The simplest of these methods employs various-sized letters on a wall chart. Obviously, patterns more complex than such a wall chart are necessary for more quantitative optical tests. A common pattern for checking resolution is a pattern of opaque lines such as stelliform on a white or transparent background. In order to determine the contrast transfer function (CTF) of an optical system, one needs precise instruments and patterns. The instant invention gives a means of easily determining CTF with a 10-20% error margin.

SUMMARY OF THE INVENTION

The pattern of the invention is an arrangement of separated and narrow uniform optical density wedges, wherein different wedges of the arrangement have different densities. This pattern allows one to readily judge the CTF of an optical path, system, or component. This is achieved by plotting contrast verus resolution for each sector. Contrast is determined by the relation of the optical density of a wedge compared to background between wedges. Resolution is related to the distance from the short side of the wedge to the obfuscation edge.

BRIEF DESCRIPTION OF THE DRAWING

The drawing shows a typical optical test pattern in accordance with the invention.

DESCRIPTION OF PREFERRED EMBODIMENT

As can be seen in the drawing, the preferred embodiment of the invention is a stelliform arrangement of sectors of uniform optical density but with different sectors of different optical densities. An alternative embodiment may have the sectors in a side-by-side tooth arrangement, such as one sees on one table of a backgammon board. Another embodiment may have sectors or teeth in opposed rows, such as the two tables of a backgammon board. Other embodiments may have two opposed rows touching or intermeshing. Moveover, not all of the stelliform arrangement of the drawing is necessary to form the invention. That is, a single quadrant of the arrangement contains all of the various optical densities. It should be understood that the term "uniform optical density" as used herein includes sectors in which the average density of any incremental area is the same as that of any other incremental area. At normal viewing or test distances such sectors appear to have uniform optical densities.

I claim:

1. An optical test pattern having wedge-shaped regions in a predetermined arrangement, wherein each of said regions is of uniform optical density but wherein different regions are of different optical densities.

2. The pattern as defined in claim 1 wherein said pattern is stelliform.

* * * * *